United States Patent
Uehara et al.

(10) Patent No.: US 7,439,377 B2
(45) Date of Patent: Oct. 21, 2008

(54) PROCESS FOR PRODUCING CONCENTRATE OF UNSATURATED FATTY ACID

(75) Inventors: Hidetaka Uehara, Yokosuka (JP); Tomomi Suganuma, Yokosuka (JP); Satoshi Negishi, Yokosuka (JP)

(73) Assignee: The Nisshin OilliO Group, Ltd., Chuo-Ku, Tokyo (JP)

( * ) Notice: Subject to any disclaimer, the term of this patent is extended or adjusted under 35 U.S.C. 154(b) by 47 days.

(21) Appl. No.: 11/723,076

(22) Filed: Mar. 16, 2007

(65) Prior Publication Data

US 2007/0173656 A1 Jul. 26, 2007

Related U.S. Application Data

(63) Continuation of application No. PCT/JP2005/017487, filed on Sep. 22, 2005.

(30) Foreign Application Priority Data

Oct. 8, 2004 (JP) .............................. 2004-296617

(51) Int. Cl.
  *C07C 51/42* (2006.01)
  *C11B 3/00* (2006.01)
(52) U.S. Cl. .................. 554/208; 554/199; 554/206
(58) Field of Classification Search .................. 554/199, 554/206, 208
  See application file for complete search history.

(56) References Cited

U.S. PATENT DOCUMENTS 6,610,868 B2 * 8/2003 Saebo et al. ................ 554/127

FOREIGN PATENT DOCUMENTS

| JP | 58-198423 A | 11/1983 |
| JP | 2001-169794 A | 6/2001 |
| JP | 2004-248671 A | 9/2004 |

| WO | 97/18320 A1 | 5/1997 |

OTHER PUBLICATIONS

Neugebauer & Co [EGER], "Linoleic acid concentrates", 1961, (Derwent Abstract).*
Ohman et al., Separation of conjugated linoleic acid isomers and parinaric fatty acid isomers by capillary electrophoresis, J. Sep. Sci., 2002, 58(8)p. 499-506.
Ma et al., Countercurrent Approach to the Enrichment of $\Delta 9c$, 11t- and $\Delta 10t$, 12c-18:2 Isomers by Urea Complexation, J. Am. Oil Chem. Soc., 2002, 79(8), p. 755-758.
Devi et al., TLC as a Tool for Quantitative Isolation of Conjugated Trienoic FA, J. Am Oil Chem. Soc., 2003, 80(4), p. 315-318.
Sehat et al., Silver-Ion High-Performance Liquid Chromatographic Separation and Identification of Conjugated Linoleic Acid Isomers, Lipids, 1998, 33(2), p. 217-221.
O. Berdeaux, et al., A simple Method of Preparation of Methyl trans 10, cis-12- and cis-9, trans-11-Octadecadienoates from Methyl Linoleate J. Am. Oil. Chem. soc., 1998, vol. 75, No. 12, pp. 1749-1755.
International Search Report for PCT/JP2005/017487 dated Sep. 22, 2005.

* cited by examiner

*Primary Examiner*—Daniel M Sullivan
*Assistant Examiner*—Yate' K Cutliff
(74) *Attorney, Agent, or Firm*—Buchanan Ingersoll & Rooney PC

(57) ABSTRACT

An easy and inexpensive process by which a concentrate of a given unsaturated fatty acid can be obtained from a mixture which has conventionally been difficult to concentrate. The process, which is for producing a concentrate of a desired isomer (a) from a mixture (A) selected from the group consisting of a mixture comprising at least two isomers of a $C_{16}$ or higher conjugated unsaturated fatty acid and a mixture comprising at least two cis-isomers of a $C_{16}$ or higher unsaturated fatty acid having a cis-double bond, is characterized by comprising: a step in which the mixture (A) is mixed with at least one $C_{4-14}$ saturated fatty acid (B) to obtain a mixture solution containing the isomer (a) dissolved therein; a crystallization step in which either crystals rich in the isomer (a) or crystals poor in the isomer (a) are precipitated from the mixture solution; and a solid-liquid separation step for obtaining the crystals rich in the isomer (a) or for obtaining a solution rich in the isomer (a) by removing the crystals poor in the isomer (a).

20 Claims, No Drawings

PROCESS FOR PRODUCING CONCENTRATE OF UNSATURATED FATTY ACID

BACKGROUND OF THE INVENTION

The present invention relates to a method for the preparation of a condensate of an unsaturated fatty acid, which permits the concentration of any unsaturated fatty acid incapable of being purified according to the currently used fractional crystallization technique.

The conjugated linoleic acid (CLA) has recently been attracted special interest since it possesses wide variety of physiological effects such as an effect of improving the metabolism of lipids, an effect of reducing the body fat, anti-cancer effect, an anti-allergic effect, and an anti-arteriosclerotic effect. The term "conjugated linoleic acid" means the generic name of fatty acids each having a conjugated double bond in the molecule and having 18 carbon atoms and a kind of fatty acid contained in meat and dairy products. It has in general been known that the conjugated linoleic acid can be prepared according to the alkali-conjugation technique (see Japanese Patent No. 3,017,108) while making use of an organic solvent represented by propylene glycol. The conjugated linoleic acid prepared according to this production method is an equimolar mixture comprising 9c,11t-conjugated linoleic acid (9-cis,11-transconjugated linoleic acid) and 10t,12c-conjugated linoleic acid (10-trans,12-cis-conjugated linoleic acid). In this respect, it has been known that these two isomers differ from one another in their physiological activities and side-effects and there has also been desired for the development of a condensate thereof which is enriched with a desired isomer.

On the other hand, as methods for the purification of fatty acids, there have been known, for instance, the fractional crystallization technique, the distillation technique, the urea adduct technique, the silver complex-forming technique, the enzymatic technique (using, for instance, a lipase). Among them, the distillation technique is a quite effective method and it has widely been used for the purification of fatty acids. However, the isomers of an unsaturated fatty acid have structures quite similar to one another and therefore, it would in general be difficult to isolate these isomers according to the distillation technique since their boiling points are very close to each other. In addition, the urea adduct method is likewise quite useful for the purification of fatty acids, but the practice thereof requires great expense and therefore, it is not suitable when the fatty acids purified by this method are used in food products. Moreover, the silver complex-forming technique is also a method quite useful for the purification of unsaturated fatty acids, but the practice thereof requires great expense and accordingly, it is likewise unfavorable when the fatty acids purified according to this method are used in food products. Furthermore, the enzymatic method requires a high production cost and it also requires the use of complicated operations. Finally, the fractional crystallization technique is a quite excellent method for the purification of fatty acids and, in general, it has widely been used, but it would be difficult to purify fatty acids having solidifying points very close to one another such as isomers of an unsaturated fatty acid.

Up to now, there have likewise variously been investigated many methods for concentrating a specific conjugated linoleic acid to thus give a condensate thereof. For instance, there has been reported a method for isolating isomers which comprises the steps of reacting a conjugated linoleic acid with, for instance, methanol under acidic conditions to form a methyl ester derivative thereof and then precipitating the same in the form of crystals (see, for instance, Non-patent Article 1 specified below). However, this method requires the use of a step for derivatization of the conjugated linoleic acid and this would result in an increase of the production cost thereof and further the resulting product must be hydrolyzed after the separation of the reaction product in this method. In case where the desired conjugated linoleic acid is concentrated through the crystallization of the reaction product, but it is difficult to obtain any concentrate thereof having a sufficiently high content of a target substance. Further, there has also been known a concentrating method through chromatography, but this method requires great expense because of the use of a solvent and a column.

There has likewise been reported a method for purifying isomers of a conjugated linoleic acid, which comprises the step of subjecting a fatty acid mixture comprising isomers of a conjugated linoleic acid or glyceride esters of the isomers to a selective reaction carried out in the presence of a lipase and in a reaction system free of any organic solvent (see, for instance, Patent Article 1 specified below). Another method has been reported, which comprises the steps of reacting a mixture containing isomers of a conjugated linoleic acid with octanol in the presence of a lipase to thus change the compositional ratio of the isomers of the conjugated linoleic acid present in the octanol ester fraction (see, for instance, Patent Article 2 specified below). Moreover, a method has likewise been reported, which comprises subjecting isomers of a conjugated linoleic acid to a selective esterification reaction with a linear higher alcohol in the presence of a lipase to thus give a 9c,11t-conjugated linoleic acid-containing fatty acid (see, for instance, Patent Article 3 specified below).

However, these methods make use of quite expensive lipases and they require the use of an additional operation (such as distillation step) for separating reaction products from un-reacted starting substances since they are ones in which any desired product is isolated based on the difference in the reactivity between each isomer of an unsaturated fatty acid with an alcohol or the difference in the susceptibility, to hydrolysis, of the derivatized isomers of an unsaturated fatty acid, observed in the presence of such lipases. In addition, regarding the derivatives of isomers, these methods further require the use of an extra operation such as an additional hydrolysis of such derivatives even after the isolation thereof. This may further increase the production cost. Moreover, the resulting product would not be favorable as an ingredient for foods depending on the kinds of alcohols used (for instance, in case wherein octanol is used as such an alcohol).

Patent Article 1: Japanese Un-Examined Patent Publication 2004-23810;

Patent Article 2: Tokuhyo Hei 11-514887;

Patent Article 3: Japanese Un-Examined Patent Publication 2001-169794; and

Non-Patent Article 1: O. Berdeaus, J. Voinot, E. Angioni, P. Jurneda and J. L. Sebedio, J. Am. Oil. Chem. Soc., 1998, 75:1749-1755.

DISCLOSURE OF THE INVENTION

Accordingly, it is an object of the present invention to provide a simple and cost-saving method which permits the production of a concentrate enriched with a specific or desired unsaturated fatty acid starting from a mixture of such unsaturated fatty acids whose concentration has conventionally been quite difficult.

It is another object of the present invention to provide a method for preparing an esterified product using the foregoing concentrate.

These and other objects of the present invention will be clearer from the following detailed description.

The inventors of this invention have conducted various studies to solve the foregoing problems associated with the conventional techniques and have succeeded in preparing a concentrate enriched with a desired isomer of a conjugated linoleic acid, by the addition of a specific saturated fatty acid to a mixture containing isomers of such a conjugated linoleic acid and the subsequent crystallization of the mixture. The inventors have thus completed the present invention on the basis of the foregoing knowledges.

According to a first aspect of the present invention, there is provided a method for preparing a concentrate which is enriched with a desired isomer (a) starting from a mixture (A) selected from the group consisting of a mixture comprising at least two isomers of a $C_{16}$ or higher conjugated unsaturated fatty acid and a mixture comprising at least two cis-isomers of a $C_{16}$ or higher unsaturated fatty acid having a double bond involved in the cis-configuration thereof, wherein the method comprises a step of mixing the mixture (A) with at least one $C_4$-$C_{14}$ saturated fatty acid (B) to thus form a mixed solution containing the desired isomer (a) dissolved therein; a crystallization and precipitation step in which crystals enriched with the isomer (a) are separated from the mixed solution or crystals having the reduced concentration of the isomer (a) are separated from the mixed solution; and a solid-liquid separation step for recovering crystals enriched with the isomer (a) or for removing the crystals having the reduced concentration of the isomer (a) to thus recover a solution enriched with the isomer (a).

According to a second aspect of the present invention, there is provided a method for preparing a concentrate which is enriched with desired isomers (a1) and (a2) starting from a mixture (A) selected from the group consisting of a mixture comprising at least three isomers of a $C_{16}$ or higher conjugated unsaturated fatty acid and a mixture comprising at least three cis-isomers of a $C_{16}$ or higher unsaturated fatty acid having a double bond involved in the cis-configuration thereof, wherein the method comprises a step of mixing the mixture (A) with at least one $C_4$-$C_{14}$ saturated fatty acid (B) to thus form a mixed solution containing the desired isomers (a1) and (a2) dissolved therein; a crystallization and precipitation step in which crystals enriched with the isomers (a1) and (a2) are separated from the mixed solution or crystals having the reduced concentration of the isomers (a1) and (a2) are separated from the mixed solution; and a solid-liquid separation step for recovering crystals enriched with the isomers (a1) and (a2) or for removing the crystals having the reduced concentration of the isomers (a1) and (a2) to thus recover a solution enriched with the isomers (a1) and (a2).

According to a third aspect of the present invention, there is provided a method for preparing a concentrate which is enriched with a desired isomer (a1) and a concentrate which is enriched with a desired isomer (a2) starting from a mixture (A) selected from the group consisting of a mixture comprising at least two isomers of a $C_{16}$ or higher conjugated unsaturated fatty acid and a mixture comprising at least two cis-isomers of a $C_{16}$ or higher unsaturated fatty acid having a double bond involved in the cis-configuration thereof, wherein the method comprises a step of mixing the mixture (A) with at least one $C_4$-$C_{14}$ saturated fatty acid (B) to thus form a mixed solution containing the desired isomers (a1) and (a2) dissolved therein; a crystallization and precipitation step in which crystals enriched with the isomer (a1) and having the reduced concentration of the isomer (a2) are separated from the mixed solution or crystals enriched with the isomer (a2) and having the reduced concentration of the isomer (a1) are separated from the mixed solution; and a solid-liquid separation step for recovering crystals enriched with the isomer (a1) and having the reduced concentration of the isomer (a2) and a solution enriched with the isomer (a2) and having the reduced concentration of the isomer (a1), or for recovering the crystals enriched with the isomer (a2) and having the reduced concentration of the isomer (a1) and a solution enriched with the isomer (a1) and having the reduced concentration of the isomer (a2).

According to a fourth aspect of the present invention, there is provided a method for preparing an esterified product comprising the step of esterifying a compound having at least one alcoholic hydroxyl group in the molecule with a concentrate of unsaturated fatty acids prepared according to the foregoing method of the present invention.

As has been discussed above, the present invention permits the preparation of a concentrate enriched with a desired unsaturated fatty acid (more specifically, a specific isomer of such a fatty acid) starting from a mixture whose concentration has conventionally been considered to be very difficult according to a cost-saving method and the method of the present invention is quite simple since it only comprises a crystallization/separation step and a step for removing solvents/middle chain fatty acids.

In addition, the resulting concentrate can be used in food products and the esters prepared using the concentrate such as mono-glycerides (MG), di-glycerides (DG) and tri-glycerides (TG) can likewise be applied to food products.

BEST MODE FOR CARRYING OUT THE INVENTION

The present invention relates to a method for preparing a concentrate which is enriched with or concentrated with respect to a desired unsaturated fatty acid and which is prepared from a specific mixture. The method of the present invention includes a step of mixing a mixture (A) selected from the group consisting of a mixture comprising at least two isomers of a $C_{16}$ or higher conjugated unsaturated fatty acid and a mixture comprising at least two cis-isomers of a $C_{16}$ or higher unsaturated fatty acid having a double bond involved in the cis-configuration thereof, with at least one $C_4$-$C_{14}$ saturated fatty acid (B) to thus form a mixed solution.

As the $C_{16}$ or higher conjugated unsaturated fatty acids included in the mixture (A), there may be listed, for instance, conjugated linoleic acids, conjugated linolenic acids (such as catalpic acid, jarcaric acid, α-calendic acid, β-calendic acid, punicic acid, and α-eleostearic acid), conjugated arachidonic acid, conjugated eicosapentaenoic acid, conjugated docosahexaenoic acid, and oxy conjugated polyenoic acid (such as dimorphenolic acid, corilic acid, artemisic acid, kamrolenic acid and licanic acid). Preferably used herein are $C_{16}$-$C_{20}$ conjugated unsaturated fatty acids, with conjugated linoleic acids being more preferred.

Examples of $C_{16}$ or higher unsaturated fatty acids each having a double bond involved in the cis-configuration thereof usable herein are hexadecenoic acids (such as palmitoleic acid), octadecenoic acids (such as oleic acid, petroselinic acid, and cis-vaccenic acid), icosenoic acid, tetracosenoic acid, hexadecadienoic acid, octadecadienoic acid (such as linoleic acid), icosadienoic acid, docosadienoic acid, hexadecatrienoic acid, octadecatrienoic acid (such as linolenic acid), icosatetraenoic acid (such as arachidonic acid), icosapentaenoic acid, docosahexaenoic acid, and unsaturated hydroxy acids (such as ricinolic acid, and oxylinolenic acid). Preferably used herein are, for instance, $C_{16}$-$C_{20}$ unsaturated fatty acids each having a double bond involved in its cis-configuration. More preferably used herein are octadecenoic acids (such as oleic acid, petroselinic acid, and cis-vaccenic acid).

The mixtures (A) used herein are those including saturated fatty acids preferably in an amount of not more than 20% by mass, further preferably not more than 10% by mass and more preferably not more than 3% by mass on the basis of the total mass of the mixture.

The saturated fatty acids (B) preferably used herein may be, for instance, $C_4$-$C_{14}$ saturated fatty acids such as butyric acid, hexanoic acid (caproic acid), octanoic acid (caprylic acid), decanoic acid (capric acid), lauric acid and myristic acid. Moreover, more preferably used herein are $C_6$-$C_{14}$ saturated fatty acids such as hexanoic acid, octanoic acid, decanoic acid, lauric acid and myristic acid. Still more preferably used herein are $C_8$ or $C_{10}$ saturated fatty acids such as octanoic acid and decanoic acid. These saturated fatty acids (B) may be used alone or in any combination of at least two of them.

When mixing the mixture (A) with at least one saturated fatty acid (B), it is preferred to prepare a mixed solution containing a desired isomer (a, a1 or a2) to be converted into a concentrate. An organic solvent may be used when mixing these components. In this respect, such organic solvent may be any one insofar as it may dissolve fatty acid at temperature lower than a boiling point of the solvent and has a melting point lower than cooling temperature of the mixture, but examples of organic solvents preferably used herein are ketones (such as acetone and methyl ethyl ketone); hydrocarbons (such as hexane and petroleum ether); aromatic hydrocarbons (such as benzene and toluene); alcohols (such as methanol, ethanol and propanol); water (moisture)-containing alcohols; ethers (such as diethyl ether); and esters (such as ethyl acetate). More preferably used herein are, for instance, acetone, hexane, alcohols and water (moisture)-containing alcohols, with acetone and hexane being most preferably used.

The mixing ratio of the mixture (A) and the at least one saturated fatty acid (B) corresponds to not less than five parts by mass of the latter (B) per 100 parts by mass of the mixture (A). More preferably, the amount of the at least one saturated fatty acid (B) ranges from 5 to 500 parts by mass and further preferably 10 to 300 parts by mass per 100 parts by mass of the mixture (A).

The method of the present invention is effective when the desired isomer (a, a1 or a2) is an unsaturated fatty acid having a cis-configuration existing at any position between 4-position and 16-position thereof. Examples of such unsaturated fatty acids each having a cis-configuration existing at any position between 4-position and 16-position thereof preferably used in the method of the present invention are conjugated linoleic acid, conjugated linolenic acid, conjugated arachidonic acid, conjugated icosapentaenoic acid, conjugated docosahexaenoic acid, oxy conjugated polyenoic acid, hexadecenoic acid (such as palmitoleic acid), octadecenoic acids (such as oleic acid, petroselinic acid, and cis-vaccenic acid), icosenoic acid, tetracosenoic acid, hexadecadienoic acid, octadecadienoic acid (such as linoleic acid), icosadienoic acid, docosadienoic acid, hexadecatrienoic acid, octadecatrienoic acid (such as linolenic acid), icosatetraenoic acid (such as arachidonic acid), icosapentaenoic acid, docosahexaenoic acid, and unsaturated hydroxy acids (such as ricinolic acid, and oxylinolenic acid). More preferably used herein are conjugated linoleic acids and octadecenoic acids and further preferably used herein are 9-cis,11-trans conjugated linoleic acid and 10-trans, 12-cis conjugated linoleic acid, oleic acid or cis-vaccenic acid. In addition, the method of the present invention is effective when the mixture (A) contains an unsaturated fatty acid whose position of the cis-configuration is different from that of the cis-configuration of the isomer (a, a1 or a2) by not less than 2 positions. Moreover, the method of the present invention is effective when the mixture (A) contains at least two kinds of conjugated fatty acids or unsaturated fatty acids each having a double bond involved in its cis-configuration. The method is more effective when the at least two kinds of conjugated fatty acids comprise at least two kinds of conjugated linoleic acids and it is most effective in cases where the at least two kinds of conjugated linoleic acids comprise 9-cis,11-trans conjugated linoleic acid and 10-trans,12-cis conjugated linoleic acid. The method is more effective when the at least two kinds of unsaturated fatty acids each having a double bond involved in its cis-configuration comprise at least two kinds of octadecenoic acids and it is most effective in cases where the at least two kinds of octadecenoic acids comprise oleic acid and cis-vaccenic acid.

The method of the present invention further comprises a crystallization and precipitation step in which crystals enriched with the isomer (a) are separated from the mixed solution or crystals having the reduced concentration of the isomer (a) are separated from the mixed solution; or a crystallization and precipitation step in which crystals enriched with the isomers (a1) and (a2) are separated from the mixed solution or crystals having the reduced concentration of the isomers (a1) and (a2) are separated from the mixed solution; or a crystallization and precipitation step in which crystals enriched with the isomer (a1) and having the reduced concentration of the isomer (a2) are separated from the mixed solution or crystals enriched with the isomer (a2) and having the reduced concentration of the isomer (a1) are separated from the mixed solution.

The term "crystals enriched with the isomer (a, a1 or a2)" herein used means that Purity of Isomer=(Amt. or Conc. of Desired Isomer (a, a1 or a2))/(Amt. or Conc. of All of the Isomers) of the crystals is higher than that of the mixture (A). In this respect, Purity of Isomer of the crystals is preferably not less than 1.2 time, more preferably not less than 1.3 time and most preferably not less than 1.5 time that of the mixture (A). In addition, the term "crystals having the reduced concentration of the isomer (a, a1 or a2)" herein used means that Purity of Isomer=(Amt. or Conc. of Desired Isomer (a, a1 or a2))/(Amt. or Conc. of All of the Isomers) of the crystals is lower than that of the mixture (A). In this connection, Purity of Isomer of the crystals is preferably not more than 0.8 time, more preferably not more than 0.7 time and most preferably not more than 0.65 time that of the mixture (A).

The crystallization and separation method usable herein may be ones similar to those currently used for treating the usual fats and fatty oils or fatty acids and may be, for instance, the crystallization and separation method through cooling. The crystallization and separation temperature may vary depending on various factors such as the kinds of unsaturated fatty acids to be concentrated and saturated fatty acids to be added as well as the presence of a solvent, and the kind and concentration thereof, but it ranges from 10 to −60° C., preferably −5 to −50° C. and more preferably −10 to −45° C., under conditions such that three volumes of acetone solvent are used, which are conditions currently used for the separation of fatty acids through cooling. Moreover, a solvent is not necessarily used in the crystallization and separation, but it is desirable to carry out the operation while adding an appropriate solvent. Examples of such solvents usable in this operation are ketones (such as acetone and methyl ethyl ketone); hydrocarbons (such as hexane and petroleum ether); aromatic hydrocarbons (such as benzene and toluene); alcohols (such as methanol, ethanol and propanol); water (moisture)-containing alcohols; ethers (such as diethyl ether); and esters (such as ethyl acetate). More preferably used herein are, for instance, acetone, hexane, alcohols and water (moisture)-containing alcohols, with acetone and hexane being most preferably used. The amount of the solvent to be added is not less than 5 parts by mass, preferably 10 to 1000 parts by mass and more preferably 50 to 500 parts by mass per 100 parts by mass of the mixed solution (the sum of the masses of the mixture (A) and the saturated fatty acid (B)).

The method of the present invention further comprises a solid-liquid separation step for recovering crystals enriched with the isomer (a) or for removing the crystals having the reduced concentration of the isomer (a) to thus recover a solution enriched with the isomer (a); or a solid-liquid separation step for recovering crystals enriched with the isomers (a1) and (a2) or for removing the crystals having the reduced concentration of the isomers (a1) and (a2) to thus recover a solution enriched with the isomers (a1) and (a2); or a solid-liquid separation step for recovering crystals enriched with the isomer (a1) and having the reduced concentration of the isomer (a2) and a solution enriched with the isomer (a2) and having the reduced concentration of the isomer (a1), or for recovering the crystals enriched with the isomer (a2) and having the reduced concentration of the isomer (a1) and a solution enriched with the isomer (a1) and having the reduced concentration of the isomer (a2). Thus, the method according to the present invention would permit a concentrate enriched with a desired isomer.

The term "solution enriched with the isomer (a, a1 or a2)" herein used means that Purity of Isomer=(Amt. or Conc. of Desired Isomer (a, a1 or a2))/(Amt. or Conc. of All of the Isomers) of the solution is higher than that of the mixture (A). In this respect, Purity of Isomer of the solution is preferably not less than 1.1 time, more preferably not less than 1.2 time and most preferably not less than 1.5 time that of the mixture (A). In addition, the term "solution having the reduced concentration of the isomer (a, a1 or a2)" herein used means that Purity of Isomer=(Amt. or Conc. of Desired Isomer (a, a1 or a2))/(Amt. or Conc. of All of the Isomers) of the solution is lower than that of the mixture (A). In this connection, Purity of Isomer of the solution is preferably not more than 0.85 time, more preferably not more than 0.7 time and most preferably not more than 0.6 time that observed for the mixture (A).

The solid-liquid separation method usable herein may be ones similar to those currently used for treating the usual fats and fatty oils or fatty acids and may be, for instance, the filtration technique, the centrifugation technique, and the sedimentation-separation technique, which may be either a batch-wise method or a continuous method.

The method of the present invention may likewise include an additional step for removing the saturated fatty acid (B) and/or the organic solvent used subsequent to the foregoing solid-liquid separation step for the removal of the saturated fatty acid (B) and/or the organic solvent present in the resulting concentrate.

The method for removing such substances which can be used herein may be ones similar to those currently used for treating the usual fats and fatty oils or fatty acids and may be, for instance, the distillation technique, the fractionation technique while making use of a surfactant and the chromatography technique, with the distillation technique being desirable in the present invention.

Further, according to the method of the present invention, the foregoing processing steps can be repeated over a desired time to thus obtain a concentrate having a high degree of concentration.

The present invention also relates to a method for preparing an esterified product which comprises the step of esterifying a compound carrying, in the molecule, at least one alcoholic hydroxyl group using the concentrate enriched with an isomer (or isomers) of an unsaturated fatty acid according to the present invention. This method will hereunder be described in detail below.

Such a compound carrying at least one alcoholic hydroxyl group in the molecule may be various kinds of compounds including, for instance, a variety of mono-alcohols, polyhydric alcohols and aminoalcohols. Specific examples thereof are polyhydric alcohols such as short chain, middle chain and long chain, saturated or unsaturated, linear or branched alcohols, glycols, glycerin and erythritols. Among these polyhydric alcohols, glycerin is preferably used in the present invention.

The esterification reaction may be carried out under conditions similar to those disclosed in, for instance, Japanese Un-Examined Patent Publication Nos. Hei 13-169795 and Hei 15-113396. By way of example, the esterification may be carried out by the addition of a lipase to a reaction system, which comprises a mixture of a compound carrying at least one alcoholic hydroxyl group in the molecule and the concentrate enriched with an isomer of an unsaturated fatty acid according to the present invention, in an amount ranging from 0.1 to 2% by mass on the basis of the total mass of the mixture and the subsequent reaction of these substances at a temperature ranging from 30 to 60° C. for a time ranging from 24 to 72 hours. At this stage, the esterification is preferably carried out while the water formed during the esterification reaction is removed by reducing the pressure of the reaction system.

The present invention will hereunder be described in more detail with reference to the following Examples, but the present invention is not restricted to these specific Examples at all. In this respect, the following are the details of the materials, analytical devices and various determination methods used in the following Examples:

1. Materials and Analytical Methods:

The materials and the analytical devices used in the following Examples are as follows:

(1) Materials (Starting Materials)

Conjugated linoleic acid CLA-80HG (available from The Nisshin OilliO Group, Ltd.);

Hexanoic acid (C6:0) (available from Tokyo Chemical Industries, Ltd.);

Octanoic acid (C8:0) (available from Tokyo Chemical Industries, Ltd.);

Decanoic acid (C10:0) (available from Tokyo Chemical Industries, Ltd.);

Lauric acid (C12:0) (available from Tokyo Chemical Industries, Ltd.);

Myristic acid (C14:0) (available from Tokyo Chemical Industries, Ltd.);

Palmitic acid (C16:0) (available from Tokyo Chemical Industries, Ltd.);

Acetone (special grade) (available from NAKARAI Tesk Co., Ltd.);

Toluene (special grade) (available from Wako Pure Chemical Industries, Ltd.);

Hexane (special grade) (available from Wako Pure Chemical Industries, Ltd.);

Ethanol (special grade) (available from Wako Pure Chemical Industries, Ltd.);

Glycerin (available from Wako Pure Chemical Industries, Ltd.);

14% Boron trifluoride methanol complex methanol solution (available from Wako Pure Chemical Industries, Ltd.);

Lipase QLM (available from Meito Sangyo Co., Ltd.);

Lipase RM (Prepared according to the method disclosed in Japanese Patent Application Serial No. 2004-114443 filed by the instant Applicant)

(2) Analytical Device

Gas Chromatograph (GC-2010) (available from Shimadzu Corporation); and

Column: DB-23 (30 m×0.25 μm×0.25 mm) (available from Agilent Technologies Corporation).

2. Analytical Methods:

(1) Method for Analyzing Isomers:

1 mL of toluene and 2 mL of a 14% boron trifluoride methanol complex methanol solution were added in 25 mg of the test sample, and the mixture was heated to 40° C. for 10 minutes. After terminating the reaction by adding 3 mL of a saturated aqueous sodium chloride solution and cooling in an ice-water bath, the resulting fatty acid methyl ester was extracted with 2 mL of hexane. The hexane extract was dried with sodium sulfate. The resulting methyl ester mixture were analyzed according to the GLC (gas-liquid chromatography) technique while making use of a column: DB-23 (30 m×0.25 μm×0.25 mm) (available from Agilent Technologies Corporation).

(2) Conditions for GLC Analysis

Instrument: GC-2010 (available from Shimadzu Corporation);

Column used: DB-23 (available from Agilent Technologies Corporation) having a size of 30 m×0.25 μm×0.25 mm;

Detector: FID;

Carrier Gas: He (flow rate of 1 mL/min);

Split Ratio: 100:1;

Column Temp.: Raising from 130° C. to 220° C. at a rate of 2° C./min;

Temp at Injection Port: 250° C.;

Temp. of Detector: 250° C.

3. Method for Concentrating Isomers

The term "purity of isomer" used in the following description means the quantity specified by the following equation:

Purity of Isomer=(Amt. or Conc. of Desired Isomer(s))/(Amt. or Conc. of All of the Isomers)

In addition, various isomers of conjugated linoleic acid will be represented by the following symbols:

9c11t: 9-cis, 11-trans conjugated linoleic acid;

10t12c: 10-trans, 12-cis conjugated linoleic acid;

9c11c: 9-cis, 11-cis conjugated linoleic acid;

10c12c: 10-cis, 12-cis conjugated linoleic acid;

tt: Sum of 9-trans,11-trans conjugated linoleic acid and 10-trans,12-trans conjugated linoleic acid In addition, various isomers of octadecenoic acid will be represented by the following symbols:

18:1: octadecenoic acid n9: oleic acid n11: cis-vaccenic acid

The starting material, conjugated linoleic acid (CLA80HG), of two different batches was used. The fatty acid compositions are listed in the following Table 1.

TABLE 1

| | Purity of Isomer | | Amt. of CLA | Composition of Fatty Acid (%) | | | | | |
|---|---|---|---|---|---|---|---|---|---|
| | 9c11t | 10t12c | | C16:0 + C18:0 | 9c 11t | 10t 12c | 9c 11c | 10c 12c | tt |
| CLA-80HG-1 | 0.46 | 0.47 | 80.5% | 7.5 | 37.2 | 38.2 | 1.2 | 1.4 | 2.5 |
| CLA-80HG-2 | 0.48 | 0.49 | 81.7% | 6.6 | 39.0 | 40.1 | 0.9 | 0.9 | 0.8 |

COMPARATIVE EXAMPLE 1

To 500 g of a conjugated linoleic acid CLA-80HG-1, there was added 1500 g of acetone to thus give a solution, followed by allowing the resulting solution to cool at −20° C. overnight with stirring. Then the solution was fractionated into a solid phase and a liquid phase through filtration under reduced pressure, followed by the removal of the acetone from the solid and liquid phases through distillation to thus give 19 g of a solid fraction 1 (Solid 1) and 480 g of a liquid fraction 1 (Liquid 1) respectively. The results of CLA isomers thus obtained are listed in the following Table 2 and the results of octadecenoic acid isomers thus obtained are listed in the following Table 3. Regarding CLA isomer, the resulting solid and liquid fractions did not undergo any change in the purity of isomers and any concentrate of a specific isomer of the foregoing acid could not be obtained. In particular, any concentrate of a specific isomer of the foregoing acid could not be obtained though the amount of the solid part was a little, so the purity improvement of isomers on this condition cannot be hoped for. Regarding octadecenoic acid isomer, the cis-vaccenic acid was concentrated (1.26 times) in the solid fraction. However, It is very difficult to improve the purity any further, because the amount of the solid fraction is very low.

TABLE 2

| Purity of Isomer | | Amt. of CLA | Composition of Fatty Acid (%) | | | | | |
|---|---|---|---|---|---|---|---|---|
| 9c11t | 10t12c | | C16:0 + C18:0 | 9c 11t | 10t 12c | 9c 11c | 10c 12c | tt |
| CLA-80HG-1 | | | | | | | | |
| 0.46 | 0.47 | 80.5% | 7.5 | 37.2 | 38.2 | 1.2 | 1.4 | 2.5 |
| Solid 1 | | | | | | | | |
| 0.39, 0.85 time | 0.48, 1.02 time | 24.2% | 67.0 | 9.4 | 11.6 | 0.4 | 0.5 | 2.3 |
| Liquid 1 | | | | | | | | |
| 0.46, 1.00 time | 0.47, 1.00 time | 85.0% | 3.4 | 39.3 | 40.4 | 1.3 | 1.5 | 2.5 |

TABLE 3

| Purity of Isomer | | Amt. of 18:1 | Composition of Fatty Acid (%) | |
|---|---|---|---|---|
| n9 | n11 | | n9 | n11 |
| CLA-80HG-1 | | | | |
| 0.926 | 0.074 | 8.1% | 7.50 | 0.60 |
| Solid 1 | | | | |
| 0.907, 0.98 time | 0.093, 1.26 time | 2.3% | 2.13 | 0.22 |
| Liquid 1 | | | | |
| 0.926, 1.00 time | 0.074, 1.00 time | 8.2% | 7.56 | 0.61 |

TABLE 5

| Purity of Isomer | | Amt. of 18:1 | Composition of Fatty Acid (%) | |
|---|---|---|---|---|
| n9 | n11 | | n9 | n11 |
| CLA-80HG-1 | | | | |
| 0.926 | 0.074 | 8.1% | 7.50 | 0.60 |
| Solid 2 | | | | |
| 0.926, 1.00 time | 0.074, 1.00 time | 6.2% | 5.72 | 0.46 |
| Liquid 2 | | | | |
| 0.925, 1.00 time | 0.075, 1.01 time | 8.9% | 8.21 | 0.67 |

COMPARATIVE EXAMPLE 2

To 20 g of a conjugated linoleic acid CLA-80HG-1, there was added 60 g of acetone to thus give a solution, followed by allowing the resulting solution to cool at −30° C. overnight. Then the solution was fractionated into a solid phase and a liquid phase through filtration under reduced pressure, followed by the removal of the acetone from the solid and liquid phases through distillation to thus give 6.7 g of a solid fraction 2 (Solid 2) and 12.5 g of a liquid fraction 2 (Liquid 2) respectively. The results of CLA isomers thus obtained are listed in the following Table 4 and the results of octadecenoic acid isomers thus obtained are listed in the following Table 5. Regarding CLA isomer, the resulting solid and liquid fractions did not undergo any change in the purity of isomers and any concentrate of a specific isomer of the foregoing acid could not be obtained. Regarding octadecenoic acid isomer, the resulting solid and liquid fractions did not undergo any change in the purity of isomers and any concentrate of a specific isomer of the foregoing acid could not be obtained.

COMPARATIVE EXAMPLE 3

Ten grams of the liquid fraction 1 prepared in Comparative Example 1 was dispensed, then dissolved in 30 g of acetone, followed by allowing the resulting solution to cool at −30° C. overnight. Then the solution was fractionated into a solid phase and a liquid phase through filtration under reduced pressure, followed by the removal of the acetone from the solid and liquid phases through distillation to thus give 4.0 g of a solid fraction 3 (Solid 3) and 5.5 g of a liquid fraction 3 (Liquid 3) respectively. The results of CLA isomers thus obtained are listed in the following Table 6 and the results of octadecenoic acid isomers thus obtained are listed in the following Table 7. Regarding CLA isomer, the resulting solid and liquid fractions did not undergo any change in the purity of isomers and any concentrate of a specific isomer of the foregoing acid could not be obtained. Regarding octadecenoic acid isomer, the resulting solid and liquid fractions did not undergo any change in the purity of isomers and any concentrate of a specific isomer of the foregoing acid could not be obtained.

TABLE 4

| Purity of Isomer | | Amt. of CLA | Composition of Fatty Acid (%) | | | | | |
|---|---|---|---|---|---|---|---|---|
| 9c11t | 10t12c | | C16:0 + C18:0 | 9c 11t | 10t 12c | 9c 11c | 10c 12c | tt |
| CLA-80HG-1 | | | | | | | | |
| 0.46 | 0.47 | 80.5% | 7.5 | 37.2 | 38.2 | 1.2 | 1.4 | 2.5 |
| Solid 2 | | | | | | | | |
| 0.53, 1.15 time | 0.43, 0.91 time | 76.7% | 14.9 | 41.0 | 33.3 | 0.5 | 0.5 | 1.4 |
| Liquid 2 | | | | | | | | |
| 0.43, 0.93 time | 0.50, 1.06 time | 84.3% | 2.6 | 36.0 | 41.9 | 1.6 | 1.8 | 3.0 |

TABLE 6

| | Purity of Isomer | | Amt. of CLA | Composition of Fatty Acid (%) | | | | | |
|---|---|---|---|---|---|---|---|---|---|
| | 9c11t | 10t12c | | C16:0 + C18:0 | 9c 11t | 10t 12c | 9c 11c | 10c 12c | tt |
| CLA80 HG-1 | 0.46 | 0.47 | 80.5 | 7.5 | 37.2 | 38.2 | 1.2 | 1.4 | 2.5 |
| Liquid 1 | 0.46 | 0.47 | 85.0% | 3.4 | 39.3 | 40.4 | 1.3 | 1.5 | 2.5 |
| Solid 3 | 0.53, 1.15 time | 0.44, 0.94 time | 86.4% | 5.1 | 45.7 | 38.1 | 0.7 | 0.7 | 1.2 |
| Liquid 3 | 0.41, 0.89 time | 0.50, 1.06 time | 83.9% | 1.6 | 34.2 | 42.3 | 1.8 | 2.1 | 3.5 |

TABLE 7

| | Purity of Isomer | | Amt. of 18:1 | Composition of Fatty Acid (%) | |
|---|---|---|---|---|---|
| | n9 | n11 | | n9 | n11 |
| Liquid 1 | 0.926 | 0.074 | 8.2% | 7.56 | 0.61 |
| Solid 3 | 0.927, 1.00 time | 0.073, 0.99 time | 6.7% | 6.22 | 0.49 |
| Liquid 3 | 0.923, 1.00 time | 0.077, 1.04 time | 9.4% | 8.66 | 0.72 |

TABLE 9

| | Purity of Isomer | | Amt. of 18:1 | Composition of Fatty Acid (%) | |
|---|---|---|---|---|---|
| | n9 | n11 | | n9 | n11 |
| CLA-80HG-2 | 0.943 | 0.057 | 8.9% | 8.36 | 0.51 |
| Solid 4 | 0.929, 0.99 time | 0.071, 1.25 time | 4.1% | 3.82 | 0.29 |
| Liquid 4 | 0.943, 1.00 time | 0.057, 1.00 time | 9.2% | 8.69 | 0.53 |

COMPARATIVE EXAMPLE 4

To 3500 g of a conjugated linoleic acid CLA-80HG-2, there was added 3500 g of acetone to thus give a solution, followed by allowing the resulting solution to cool at −15° C. overnight with stirring. Then the solution was fractionated into a solid phase and a liquid phase through filtration under reduced pressure, followed by the removal of the acetone from the solid and liquid phases through distillation to thus give 230 g of a solid fraction 4 (Solid 4) and 3260 g of a liquid fraction 4 (Liquid 4) respectively. The results of CLA isomers thus obtained are listed in the following Table 8 and the results of octadecenoic acid isomers thus obtained are listed in the following Table 9. Regarding CLA isomer, the resulting solid and liquid fractions did not undergo any change in the purity of isomers and any concentrate of a specific isomer of the foregoing acid could not be obtained. Regarding octadecenoic acid isomer, the cis-vaccenic acid was concentrated (1.25 times) in the solid fraction. However, It is very difficult to improve the purity any further, because the amount of the solid fraction is very low.

(ii) Method for the Concentration of Isomers

EXAMPLE 1

To the liquid fraction 1 (Liquid 1) prepared in Comparative Example 1, there were added various kinds of saturated fatty acids and acetone to thus prepare a variety of mixed solutions (sample solutions), followed by allowing these solutions to stand overnight with cooling. Then each sample solution was separated into a solid fraction and a liquid fraction through decantation and then the acetone was removed from these solid and liquid fractions through distillation. The following Table 10 shows the conditions used for the crystallization and separation and the results concerning yields thus obtained. In addition, Table 11 given below shows results obtained or the purity of isomers and the compositions of fatty acids. Regarding the solid fractions, there were observed significant differences in the purities of isomers of octanoic acid, decanoic

TABLE 8

| | Purity of Isomer | | Amt. of CLA | Composition of Fatty Acid (%) | | | | | |
|---|---|---|---|---|---|---|---|---|---|
| | 9c11t | 10t12c | | C16:0 + C18:0 | 9c 11t | 10t 12c | 9c 11c | 10c 12c | tt |
| CLA 80HG-2 | 0.48 | 0.49 | 81.7% | 6.6 | 39.0 | 40.1 | 0.9 | 0.9 | 0.8 |
| Solid 4 | 0.42, 0.88 time | 0.52, 1.06 time | 37.5% | 52.5 | 15.8 | 19.6 | 0.5 | 0.5 | 1.2 |
| Liquid 4 | 0.48, 1.00 time | 0.49, 1.00 time | 84.6% | 3.5 | 40.5 | 41.5 | 0.9 | 0.9 | 0.8 | acid, lauric acid and myristic acid. More specifically, a concentrate enriched with a 9c11t isomer was prepared when using octanoic acid as the saturated fatty acid, while concentrates enriched with 10t12c isomers were obtained when using decanoic acid, lauric acid and myristic acid as the saturated fatty acid components. In other words, among the isomers of octanoic acid, one concentrated in the solid fraction was found to be the 9c11t isomer thereof, while among the isomers of decanoic acid, lauric acid or myristic acid, one concentrated in the solution fractions were found to be the 10t12c isomers thereof. When investigating the added fatty acids included in the solid fraction, the content of the octanoic acid was found to be 3.3% which was extremely low as compared with those observed for the remaining fatty acids. More specifically, there was observed a correlation between the precipitated amount of the added fatty acid and the kinds of the isomers thereof. Regarding the liquid fractions, there were observed significant changes in the purities of isomers when using octanoic acid and decanoic acid as the saturated fatty acids. More specifically, a concentrate enriched with a 10t12c isomer was obtained when using octanoic acid as the saturated fatty acid component, while a concentrate enriched with a 9c11t isomer was prepared when using decanoic acid as the saturated fatty acid component.

TABLE 10

| | Kind of saturated fatty acid | Added amt. (g) of saturated fatty acid | Added amt. of Liquid 1 (g) | Added amt. of acetone (g) | Cooling Temp. (° C.) | Yield (g) Solid fraction | Yield (g) Liquid fraction |
|---|---|---|---|---|---|---|---|
| 1 | C8:0 | 2 | 8 | 30 | −30 | 2.0 | 7.9 |
| 2 | C10:0 | 5 | 5 | 30 | −40 | 5.3 | 4.7 |
| 3 | C12:0 | 3 | 7 | 30 | −20 | 1.9 | 8.0 |
| 4 | C14:0 | 2 | 8 | 30 | −30 | 2.7 | 7.2 |
| 5 | C16:0 | 2 | 8 | 30 | 4 | 1.9 | 7.8 |

TABLE 11

| | | Purity of Isomer | | |
|---|---|---|---|---|
| Added fatty acid | | 9c11t | 10t12c | CLA (%) |
| Liquid 1 | | 0.46 | 0.47 | 85.0 |
| Comparative | S | 0.53, 1.15 time | 0.44, 0.94 time | 86.4 |
| Example 3 | L | 0.41, 0.89 time | 0.50, 1.06 time | 83.9 |
| C8:0 | S | 0.66, 1.43 time | 0.31, 0.66 time | 79.3 |
| | L | 0.39, 0.85 time | 0.53, 1.13 time | 65.3 |
| C10:0 | S | 0.30, 0.65 time | 0.65, 1.38 time | 37.3 |
| | L | 0.62, 1.35 time | 0.31, 0.66 time | 45.8 |
| C12:0 | S | 0.28, 0.61 time | 0.66, 1.40 time | 23.5 |
| | L | 0.48, 1.04 time | 0.46, 0.98 time | 67.7 |
| C14:0 | S | 0.32, 0.70 time | 0.61, 1.30 time | 29.0 |
| | L | 0.49, 1.07 time | 0.46, 0.98 time | 81.3 |
| C16:0 | S | 0.45, 0.98 time | 0.48, 1.02 time | 24.3 |
| | L | 0.47, 1.02 time | 0.47, 1.00 time | 78.7 |

TABLE 11-continued

| | | Composition of Fatty Acid (%) | | | | | |
|---|---|---|---|---|---|---|---|
| Added fatty acid | | Fatty acid added | C16:0 + C18:0 | 9c11t | 10t12c | 9c11c | 10c12c | tt |
| Liquid 1 | | — | | 3.4 | 39.3 | 40.4 | 1.3 | 1.5 | 2.5 |
| Comp. Ex. 3 | S | | | 5.1 | 45.7 | 38.1 | 0.7 | 0.7 | 1.2 |
| | L | | | 1.6 | 34.2 | 42.3 | 1.8 | 2.1 | 3.5 |
| C8:0 | S | 3.0 | | 9.5 | 52.7 | 24.5 | 0.4 | 0.4 | 1.3 |
| | L | 23.9 | | 1.0 | 25.6 | 34.9 | 1.2 | 1.3 | 2.3 |
| C10:0 | S | 56.5 | | 2.2 | 11.2 | 24.3 | 0.4 | 0.5 | 0.9 |
| | L | 45.3 | | 0.8 | 28.5 | 14.1 | 0.8 | 0.9 | 1.5 |
| C12:0 | S | 67.3 | | 5.9 | 6.6 | 15.5 | 0.2 | 0.4 | 0.8 |
| | L | 21.4 | | 1.3 | 32.7 | 31.0 | 1.0 | 1.1 | 1.9 |
| C14:0 | S | 58.5 | | 8.7 | 9.2 | 17.6 | 0.4 | 0.5 | 1.3 |
| | L | 6.3 | | 1.0 | 39.5 | 37.1 | 1.2 | 1.3 | 2.2 |
| C16:0 | S | 70.7 | | 1.2 | 11.0 | 11.7 | 0.3 | 0.4 | 0.9 |
| | L | 10.1 | | 0.4 | 36.7 | 37.3 | 1.2 | 1.3 | 2.2 |

Note: In the composition of fatty acid which contains C16:0, the amount of C16:0 is specified in the column entitled "Fatty acid added", while the amount of C18:0 is specified in the column entitled "C16:0+C18:0". The symbols "S" and "L" appearing in the column entitled "Added fatty acid" means "solid fraction" and "liquid fraction", respectively.

EXAMPLE 2

To a mixture containing 8.0 g of the liquid fraction 4 (Liquid 4) prepared in Comparative Example 4 and 2.0 g of hexanoic acid, there was added 30 g of acetone to thus form a mixed solution and the resulting solution was cooled at −30° C. overnight. Then the solution was fractionated into a solid phase and a liquid phase through decantation, followed by the removal of the acetone from the solid and liquid phases through distillation to thus give 1.7 g of a solid fraction 5 (Solid 5) and 8.2 g of a liquid fraction 5 (Liquid 5) respectively. The results thus obtained are listed in the following Table 12. The purities of isomers observed for the solid fraction was considerably changed, the 9c11t isomer was concentrated in the solid fraction, while the 10t12c isomer was concentrated in the liquid fraction to thus give each corresponding isomer-containing concentrate. As well as the case of octanoic acid in Example 1, when investigating the added fatty acids included in the solid fraction, the content of the hexanoic acid was found to be 0.4% which was extremely low as compared with those observed for the remaining fatty acids.

TABLE 12

| | Purity of isomer | | Composition of Fatty Acid (%) | | | | | | | |
|---|---|---|---|---|---|---|---|---|---|---|
| | 9c11t | 10t 12c | CLA (%) | C6:0 | C16:0 + C18:0 | 9c 11t | 10t 12c | 9c 11c | 10c 12c | tt |
| Liquid 4 | 0.48 | 0.49 | 84.6 | — | 3.5 | 40.5 | 41.5 | 0.9 | 0.9 | 0.8 |
| Solid 5 | 0.64, 1.33 time | 0.34, 0.69 time | 80.9 | 0.4 | 8.7 | 52.1 | 27.6 | 0.4 | 0.4 | 0.5 |
| Liquid 5 | 0.39, 0.81 time | 0.52, 1.08 time | 72.2 | 15.1 | 2.2 | 31.8 | 37.7 | 0.9 | 0.9 | 0.9 |

EXAMPLE 3

To the liquid fraction 4 (Liquid 4) prepared in Comparative Example 4, there were added decanoic acid and acetone to thus prepare a variety of mixed solutions (sample solutions), followed by allowing these solutions to cool for three hours with stirring. Then each sample solution was separated into a solid fraction and a liquid fraction through filtration under reduced pressure and then the acetone was removed from these solid and liquid fractions through distillation. The following Table 13 shows the conditions used for the crystallization and separation and the results concerning yields thus obtained. In addition, Table 14 given below shows results obtained or the purity of isomers and the compositions of fatty acids.

The 10t12c isomer was concentrated in the solid fraction with liquid 4/decanoic acid ratios of 7/3, 6/4, 5/5, 4/6, 3/7 and 2/8. In particular, the purities of isomers observed for the solid fraction was considerably changed with liquid 4, decanoic acid ratios of 7/3, 6/4, 5/5 and 4/6. The 9c11t isomer was concentrated in the liquid fraction with liquid 4/decanoic acid ratios of 7/3, 6/4, 5/5 and 4/6. In particular, the purities of isomers observed for the liquid fraction was considerably changed with liquid 4/decanoic acid ratios of 6/4, 5/5 and 4/6. With the liquid 4/decanoic acid ratios of 5/5, the purity of 10t12c was decreased when the cooling temperature was reduced. As a result, the purity of 9c11t was increased.

TABLE 13

| | Ratios of Liquid 4 / Decanoic acid | Added amt. (g) of Liquid 4 | Added amt. (g) of Decanoic acid | Added amt. of acetone (g) | Cooling Temp. (° C.) | Yield (g) Solid fraction | Yield (g) Liquid fraction |
|---|---|---|---|---|---|---|---|
| 1 | 7/3 | 70 | 30 | 300 | −33 | 17.3 | 81.9 |
| 2 | 6/4 | 60 | 40 | 300 | −31 | 30.2 | 68.8 |
| 3 | 5/5 | 50 | 50 | 300 | −32 | 28.3 | 69.2 |
| 4 | 5/5 | 50 | 50 | 300 | −34 | 53.3 | 46.2 |
| 5 | 4/6 | 40 | 60 | 300 | −30 | 34.1 | 64.1 |
| 6 | 3/7 | 30 | 70 | 300 | −25 | 17.5 | 82.2 |
| 7 | 2/8 | 20 | 80 | 300 | −20 | 22.4 | 76.8 |

TABLE 14

| Ratios of Liquid 4 / Decanoic acid | | Purity of Isomer | | CLA (%) |
|---|---|---|---|---|
| | | 9c11t | 10t12c | |
| Liquid 4 | | 0.48 | 0.49 | 84.6 |
| Liquid 1 | | 0.46 | 0.47 | 85.0 |
| Comparative Example 3 | S | 0.53, 1.15 time | 0.44, 0.94 time | 86.4 |
| | L | 0.41, 0.89 time | 0.50, 1.06 time | 83.9 |
| 1. 7/3 | S | 0.21, 0.44 time | 0.76, 1.55 time | 53.6 |
| | L | 0.53, 1.10 time | 0.44, 0.90 time | 61.1 |
| 2. 6/4 | S | 0.21, 0.44 time | 0.77, 1.57 time | 54.6 |
| | L | 0.61, 1.27 time | 0.35, 0.71 time | 50.8 |
| 3. 5/5 | S | 0.21, 0.44 time | 0.77, 1.57 time | 38.1 |
| | L | 0.58, 1.21 time | 0.38, 0.76 time | 47.2 |
| 4. 5/5 | S | 0.28, 0.58 time | 0.70, 1.43 time | 39.8 |
| | L | 0.70, 1.46 time | 0.26, 0.53 time | 45.1 |
| 5. 4/6 | S | 0.21 0.44 time | 0.77, 1.57 time | 23.2 |
| | L | 0.57, 1.19 time | 0.39, 0.80 time | 40.5 |
| 6. 3/7 | S | 0.31, 0.65 time | 0.65, 1.33 time | 13.1 |
| | L | 0.49, 1.02 time | 0.47, 0.96 time | 29.4 |
| 7. 2/8 | S | 0.36, 0.75 time | 0.60, 1.22 time | 6.8 |
| | L | 0.49, 1.02 time | 0.48, 0.98 time | 19.0 |

| Ratios of Liquid 4 / Decanoic acid | | Fatty acid added | Composition of Fatty Acid (%) | | | | | |
|---|---|---|---|---|---|---|---|---|
| | | | C16:0 + C18:0 | 9c11t | 10t12c | 9c11c | 10c12c | tt |
| Liquid 4 | | — | 3.5 | 40.5 | 41.5 | 0.9 | 0.9 | 0.8 |
| Liquid 1 | | — | 3.4 | 39.3 | 40.4 | 1.3 | 1.5 | 2.5 |
| Comp. Ex. 3 | S | — | 5.1 | 45.7 | 38.1 | 0.7 | 0.7 | 1.2 |
| | L | — | 1.6 | 34.2 | 42.3 | 1.8 | 2.1 | 3.5 |
| 1. 7/3 | S | | 33.2 | 7.9 | 11.4 | 40.7 | 0.4 | 0.5 | 0.5 |
| | L | | 28.3 | 1.4 | 32.4 | 26.6 | 0.8 | 0.7 | 0.7 |
| 2. 6/4 | S | | 35.5 | 4.9 | 11.5 | 41.8 | 0.3 | 0.5 | 0.5 |
| | L | | 39.5 | 0.9 | 31.0 | 17.8 | 0.7 | 0.6 | 0.6 |
| 3. 5/5 | S | | 54.9 | 3.5 | 7.9 | 29.2 | 0.3 | 0.4 | 0.4 |
| | L | | 44.0 | 1.1 | 27.5 | 17.9 | 0.6 | 0.6 | 0.5 |

TABLE 14-continued

| | | | | | | | | |
|---|---|---|---|---|---|---|---|---|
| 4. 5/5 | S | 53.8 | 2.8 | 10.9 | 27.9 | 0.3 | 0.3 | 0.4 |
| | L | 45.3 | 0.8 | 31.3 | 11.8 | 0.8 | 0.7 | 0.6 |
| 5. 4/6 | S | 72.5 | 2.2 | 4.8 | 17.8 | 0.2 | 0.2 | 0.3 |
| | L | 51.8 | 1.1 | 23.0 | 15.9 | 0.5 | 0.5 | 0.5 |
| 6. 3/7 | S | 83.4 | 1.7 | 4.1 | 8.5 | 0.1 | 0.2 | 0.2 |
| | L | 65.5 | 1.0 | 14.5 | 13.9 | 0.4 | 0.3 | 0.3 |
| 7. 2/8 | S | 91.5 | 0.8 | 2.4 | 4.1 | 0.1 | 0.1 | 0.1 |
| | L | 77.4 | 0.7 | 9.3 | 9.0 | 0.2 | 0.2 | 0.2 |

EXAMPLE 4

To a liquid fraction 4 (Liquid 4) prepared in Comparative Example 4 and decanoic acid mixture (solute) with liquid 4/decanoic acid ratio of 6/4, there was added acetone (solvent) to thus form a mixed solution and the resulting solution was cooled for 3 hours with stirring. Then each sample solution was separated into a solid fraction and a liquid fraction through filtration under reduced pressure and then the acetone was removed from these solid and liquid fractions through distillation. The following Table 15 shows the conditions used for the crystallization and separation and the results concerning yields thus obtained. In addition, Table 16 given below shows results obtained or the purity of isomers and the compositions of fatty acids.

With all solute to solvent (acetone) ratios (Solute/Acetone), the 10t12c isomer was concentrated in the solid fraction and the 9c11t isomer was concentrated in the liquid fraction.

TABLE 15

| Ratios of Solute / Acetone | Added amt. (g) of Liquid 4 | Added amt. (g) of Decanoic acid | Added amt. of acetone (g) | Cooling Temp. (° C.) | Yield (g) Solid fraction | Yield (g) Liquid fraction |
|---|---|---|---|---|---|---|
| 1  1/2 | 80 | 53 | 266 | −27 | 46.1 | 86.4 |
| 2  1/1 | 120 | 80 | 200 | −21 | 105.2 | 86.4 |

Note: The word "Solute" means the total amount of liquid 4 and decanoic acid.

TABLE 16

| Ratios of Liquid 4 / Decanoic acid | | Purity of Isomer | | |
|---|---|---|---|---|
| | | 9c11t | 10t12c | CLA (%) |
| Liquid 4 | | 0.48 | 0.49 | 84.6 |
| 1. 1/2 | S | 0.23, 0.48 time | 0.75, 1.53 time | 54.7 |
| | L | 0.63, 1.31 time | 0.33, 0.67 time | 54.9 |
| 2. 1/1 | S | 0.34, 0.71 time | 0.63, 1.28 time | 53.9 |
| | L | 0.63, 1.31 time | 0.34, 0.69 time | 54.2 |

| Ratios of Liquid 4 / Decanoic acid | | Composition of Fatty Acid (%) | | | | | |
|---|---|---|---|---|---|---|---|
| | | Fatty acid added | C16:0 + C18:0 | 9c11t | 10t12c | 9c11c | 10c12c | tt |
| Liquid 4 | | — | 3.5 | 40.5 | 41.5 | 0.9 | 0.9 | 0.8 |
| 1. 1/2 | S | 35.5 | 4.8 | 12.4 | 41.2 | 0.3 | 0.5 | 0.4 |
| | L | 34.5 | 0.9 | 34.5 | 18.3 | 0.8 | 0.7 | 0.6 |
| 2. 1/1 | S | 36.6 | 3.2 | 18.3 | 34.1 | 0.5 | 0.5 | 0.5 |
| | L | 34.9 | 1.3 | 33.9 | 18.3 | 0.8 | 0.7 | 0.6 |

EXAMPLE 5

To a liquid fraction 4 (Liquid 4) prepared in Comparative Example 4 and decanoic acid mixture, there was added various kind of solvent to thus form a mixed solution and the resulting solution was stand overnight with cooling. Then each sample solution was separated into a solid fraction and a liquid fraction decantation and then the solvent was removed from these solid and liquid fractions through distillation. The following Table 17 shows the conditions used for the crystallization and separation and the results concerning yields thus obtained. In addition, Table 18 given below shows results obtained or the purity of isomers and the compositions of fatty acids.

With all solvents used, the 10t12c isomer was concentrated in the solid fraction.

TABLE 17

| | Kind of Solvent | Added amt. (g) of Liquid 4 | Added amt. (g) of Decanoic acid | Added amt. of acetone (g) | Cooling Temp. (° C.) | Yield (g) Solid fraction | Yield (g) Liquid fraction |
|---|---|---|---|---|---|---|---|
| 1 | Hexane | 6 | 4 | 30 | −25 | 2.0 | 7.9 |
| 2 | Ethanol | 12 | 8 | 20 | −25 | 2.8 | 17.1 |
| 3 | Ethanol (10% water) | 6 | 4 | 30 | −32 | 1.9 | 8.0 |

Ethanol (10% water): Ethanol includes 10% water

TABLE 18

| Kind of Solvent | | Purity of Isomer | | |
|---|---|---|---|---|
| | | 9c11t | 10t12c | CLA (%) |
| Liquid 4 | | 0.48 | 0.49 | 84.6 |
| 1. Hexane | S | 0.27, 0.56 time | 0.71, 1.45 time | 57.4 |
| | L | 0.53, 1.10 time | 0.43, 0.88 time | 54.6 |
| 2. Ethanol | S | 0.37, 0.77 time | 0.60, 1.22 time | 56.0 |
| | L | 0.50, 1.04 time | 0.47, 0.96 time | 53.4 |
| 3. Ethanol (10% water) | S | 0.31, 0.65 time | 0.66, 1.35 time | 56.5 |
| | L | 0.52, 1.08 time | 0.45, 0.92 time | 53.0 |

| Kind of Solvent | | Composition of Fatty Acid (%) | | | | | | |
|---|---|---|---|---|---|---|---|---|
| | | Fatty acid added | C16:0 + C18:0 | 9c11t | 10t12c | 9c11c | 10c12c | tt |
| Liquid 4 | | — | 3.5 | 40.5 | 41.5 | 0.9 | 0.9 | 0.8 |
| 1. Hexane | S | 36.2 | 2.0 | 15.6 | 40.5 | 0.4 | 0.5 | 0.5 |
| | L | 34.4 | 2.3 | 28.9 | 23.7 | 0.7 | 0.7 | 0.6 |
| 2. Ethanol | S | 33.3 | 2.8 | 20.7 | 33.6 | 0.5 | 0.6 | 0.6 |
| | L | 33.9 | 2.1 | 26.5 | 25.1 | 0.6 | 0.6 | 0.6 |
| 3. Ethanol (10% water) | S | 34.1 | 3.7 | 17.7 | 37.4 | 0.4 | 0.5 | 0.5 |
| | L | 36.6 | 1.9 | 27.6 | 23.6 | 0.6 | 0.6 | 0.6 |

EXAMPLE 6

To a mixture containing 90 g of liquid fraction 4 (Liquid 4) prepared in Comparative Example 4 and 10 g of octanoic acid, there was added 300 g of acetone to thus form a mixed solution and the resulting solution was cooled at −25° C. for 10 hours with stirring. Then the solution was fractionated into a solid phase and a liquid phase through filtration under reduced pressure, followed by the removal of the acetone from the solid and liquid phases through distillation to thus give 19 g of a solid fraction 6 (Solid 6) and 78 g of a liquid fraction 6 (Liquid 6) respectively. The results thus obtained are listed in the following Table 19.

The purities of isomers observed for the both solid and liquid fractions were considerably changed, the 9c11t isomer was remarkably concentrated in the solid fraction, while the 10t12c isomer was concentrated in the liquid fraction to thus give each corresponding isomer-containing concentrate.

TABLE 19

| | Purity of isomer | | | Composition of Fatty Acid (%) | | | | | |
|---|---|---|---|---|---|---|---|---|---|---|
| | 9c11t | 10t12c | CLA (%) | C8:0 | C16:0 + C18:0 | 9c 11t | 10t 12c | 9c 11c | 10c 12c | tt |
| L 4 | 0.48 | 0.49 | 84.6 | — | 3.5 | 40.5 | 41.5 | 0.9 | 0.9 | 0.8 |
| S 6 | 0.75, 1.56 time | 0.24, 0.49 time | 75.6 | 3.0 | 11.6 | 56.5 | 17.8 | 0.4 | 0.4 | 0.5 |
| L 6 | 0.41, 0.85 time | 0.55, 1.12 time | 77.6 | 9.5 | 1.3 | 32.0 | 42.8 | 1.0 | 1.0 | 0.9 |

L 4: Liquid (fraction) 4;
S 6: Solid (fraction) 6; and
L 6: Liquid (fraction) 6.

EXAMPLE 7

To a mixture containing 100 g of liquid fraction 1 (Liquid 1) prepared in Comparative Example 1 and 100 g of decanoic acid, there was added 600 g of acetone to thus form a mixed solution and the resulting solution was cooled at −35° C. for 3 hours with stirring. Then the solution was fractionated into a solid phase and a liquid phase through filtration under reduced pressure, followed by the removal of the acetone from the solid and liquid phases through distillation to thus give 105 g of a solid fraction 7 (Solid 7) and 95 g of a liquid fraction 7 (Liquid 7) respectively. The results thus obtained are listed in the following Table 20. The purities of isomers observed for the both solid and liquid fractions were considerably changed, the 10t12c isomer was remarkably concentrated in the solid fraction, while the 9c11t isomer was concentrated in the liquid fraction to thus give each corresponding isomer-containing concentrate.

EXAMPLE 8

Decanoic acid was removed from 70 g of the solid fraction 7 (Solid 7) prepared in Example 7 through distillation at the temperature of 100 to 150° C. and at a degree of vacuum of 3 Torr to thus give 31 g of Concentrate 1. The results are listed in the following Table 21. After the removal of medium chain fatty acids, the purity of isomers observed for the Concentrate 1 was not changed, and thus decomposition and isomerization were not found. As compared to CLA80HG-1, the purity of 10t12c isomer observed for Concentrate 1 increases to 1.44 time that of CLA80HG-1, while the concentration of conjugated fatty acids decreases inconsiderably. This is because palmitic acid and stearic acid were concentrated in the solid fraction. It is desirable that saturated fatty acids contained in a sample to be concentrated are lower.

TABLE 20

| | Purity of isomer | | | | Composition of Fatty Acid (%) | | | | | |
|---|---|---|---|---|---|---|---|---|---|---|
| | 9c11t | 10t 12c | CLA (%) | C10:0 | C16:0 + C18:0 | 9c 11t | 10t 12c | 9c 11c | 10c 12c | tt |
| L 1 | 0.46 | 0.47 | 85.0 | — | 3.4 | 39.3 | 40.4 | 1.3 | 1.5 | 2.5 |
| S 7 | 0.24, 0.52 time | 0.71, 1.51 time | 33.9 | 56.5 | 6.1 | 8.2 | 24.0 | 0.3 | 0.5 | 0.9 |
| L 7 | 0.65, 1.41 time | 0.28, 0.60 time | 44.4 | 47.1 | 0.7 | 28.9 | 12.3 | 0.9 | 0.8 | 1.5 |

L 1: Liquid (fraction) 1;
S 7: Solid (fraction) 7; and
L 7: Liquid (fraction) 7.

TABLE 21

| | Purity of 10t12c isomer | CLA (%) | Composition of Fatty Acid (%) | | | | | | |
|---|---|---|---|---|---|---|---|---|---|
| | | | C10:0 | C16:0 + C18:0 | 9c11t | 10t12c | 9c11c | 10c12c | tt |
| CLA80HG-1 | 0.47 | 80.5 | | 7.5 | 32.2 | 38.2 | 1.2 | 1.4 | 2.5 |
| Solid 7 | 0.71 | 33.9 | 56.5 | 6.1 | 8.2 | 24.0 | 0.3 | 0.5 | 0.9 |
| Concentrate 1 | 0.71 | 75.2 | 4.2 | 12.7 | 17.8 | 53.6 | 0.7 | 1.1 | 2.0 |

EXAMPLE 9

Decanoic acid was removed from 70 g of the liquid fraction 7 (Liquid 7) prepared in Example 7 through distillation at the temperature of 100 to 150° C. and at a degree of vacuum of 3 Torr to thus give 31.5 g of Concentrate 2. The results are listed in the following Table 22. After the removal of medium chain fatty acids, the purity of isomers observed for the Concentrate 2 was not changed, and thus decomposition and isomerization were not found. As compared to CLA80HG-1, the purity of 9c11t isomer observed for Concentrate 2 increases to 1.44 time that of CLA80HG-1.

from the solid and liquid phases through distillation to thus give 53 g of a solid fraction 8 (Solid 8) and 46 g of a liquid fraction 8 (Liquid 8), respectively. The concentration results for CLA isomer are listed in the following Table 23 and the concentration results for octadecenoic acid isomer are listed in the following Table 24.

Regarding CLA isomer, The purities of isomers observed for both the solid fraction and the liquid fraction were considerably changed, the 10t12c isomer was concentrated in the solid fraction, while the 9c11t isomer was concentrated in the liquid fraction to thus give each corresponding isomer-containing concentrate.

Regarding octadecenoic acid isomer, the purity of cis-vaccenic acid (n11) observed for the solid fraction was considerably upgraded (1.79 time). Although the yield of the solid fraction is very high (not less than 50%), the upgrading rate is higher than the upgrading rates obtained in Comparative Examples 1 and 4 (1.26 time).

TABLE 22

| | Purity of 9c11t isomer | CLA (%) | Composition of Fatty Acid (%) | | | | | | |
|---|---|---|---|---|---|---|---|---|---|
| | | | C10:0 | C16:0 + C18:0 | 9c11 t | 10t12c | 9c11c | 10c12c | tt |
| CLA80HG-1 | 0.47 | 80.5 | | 7.5 | 32.2 | 38.2 | 1.2 | 1.4 | 2.5 |
| Liquid 7 | 0.65 | 44.4 | 47.1 | 0.7 | 28.9 | 12.3 | 0.9 | 0.8 | 1.5 |
| Concentrate 2 | 0.65 | 82.2 | 1.0 | 1.3 | 53.5 | 22.9 | 1.7 | 1.5 | 2.6 |

EXAMPLE 10

To a mixture containing 50 g of the liquid fraction 4 (Liquid 4) prepared in Comparative Example 4 and 50 g of decanoic acid, there was added 300 g of acetone to thus form a mixed solution and the resulting solution was cooled at −35° C. for 3 hour with stirring. Then the solution was fractionated into a solid phase and a liquid phase through filtration under reduced pressure, followed by the removal of the acetone

TABLE 23

| | Purity of isomer | | CLA (%) | Composition of Fatty Acid (%) | | | | | | |
|---|---|---|---|---|---|---|---|---|---|---|
| | 9c11t | 10t12c | | C10:0 | C16:0 + C18:0 | 9c11t | 10t12c | 9c11c | 10c12c | tt |
| Liquid 4 | 0.48 | 0.49 | 84.6 | — | 3.5 | 40.5 | 41.5 | 0.9 | 0.9 | 0.8 |
| Solid 8 | 0.28, 0.58 time | 0.70, 1.43 time | 39.8 | 53.8 | 2.8 | 10.9 | 27.9 | 0.3 | 0.3 | 0.4 |
| Liquid 8 | 0.70, 1.46 time | 0.26, 0.53 time | 45.1 | 45.3 | 0.8 | 31.3 | 11.8 | 0.8 | 0.7 | 0.6 |

TABLE 24

| | Purity of isomer | | | Composition of Fatty Acid (%) | | |
|---|---|---|---|---|---|---|
| | n9 | n11 | 18:1 (%) | C10:0 | N9 | N11 |
| Liquid 4 | 0.943 | 0.057 | 9.2 | | 8.7 | 0.5 |
| Solid 8 | 0.898, 0.95 time | 0.102, 1.79 time | 2.9 | 53.8 | 2.56 | 0.29 |
| Liquid 8 | 0.961, 1.02 time | 0.039, 0.68 time | 7.1 | 45.3 | 6.80 | 0.28 |

EXAMPLE 11

To 53 g of the solid fraction 8 (Solid 8) prepared in Example 10, there was added 159 g of acetone to thus form a mixed solution and the resulting solution was cooled at −35° C. for 3 hour with stirring. Then the solution was fractionated into a solid phase and a liquid phase through filtration under reduced pressure, followed by the removal of the acetone from the solid and liquid phases through distillation to thus give 15 g of a solid fraction 9 (Solid 9) and 37 g of a liquid fraction 9 (Liquid 9), respectively. The results thus obtained are listed in the following Table 25. The purities of isomers observed for both the solid fraction and the liquid fraction was changed, the 10t12c isomer was concentrated in the solid fraction, while the 9c11t isomer was concentrated in the liquid fraction. After the crystallization step and the solid-liquid separation step were repeated, the purity of 10t12c isomer observed for the solid fraction was further upgraded and the 10t12c isomer was highly concentrated in the solid fraction (1.73 time).

TABLE 25

| | Purity of isomer | | CLA | Composition of Fatty Acid (%) | | | | | | | |
|---|---|---|---|---|---|---|---|---|---|---|---|
| | | | | | C16:0 + | | | | | | |
| | 9c11t | 10t12c | (%) | C10:0 | C18:0 | 9c11t | 10t12c | 9c11c | 10c12c | tt |
| Liquid 4 | 0.48 | 0.49 | 84.6 | | 3.5 | 40.5 | 41.5 | 0.9 | 0.9 | 0.8 |
| Solid 8 | 0.28 | 0.70 | 39.8 | 53.8 | 2.8 | 10.9 | 27.9 | 0.3 | 0.3 | 0.4 |
| Solid 9 | 0.13, 0.46 time (0.27) | 0.85, 1.21 time (1.73) | 42.8 | 49.6 | 4.8 | 5.6 | 36.4 | 0.2 | 0.3 | 0.4 |
| Liquid 9 | 0.35, 1.25 time (0.73) | 0.62, 0.89 time (1.27) | 37.4 | 56.7 | 1.9 | 13.0 | 23.4 | 0.3 | 0.4 | 0.4 |

Note: scale factor of improving the purity of isomer compared to Liquid 4 are in parentheses.

EXAMPLE 12

To a reaction container equipped with a stirring machine, there were added 2 g of glycerin and 18 g of the conjugated fatty acid mixture prepared in Example 4, followed by the addition of 40 mg of Lipase QLM and 160 mg of Lipase RM with stirring. The reaction of these components was carried out at 60° C. and a pressure of 10 Torr over 24 hours to thus form 18 g of a triglyceride. The resulting triglyceride was found to have a triglyceride concentration of 95% and an acid value of 3.1.

What is claimed is:

1. A method for preparing a concentrate which is enriched with a desired isomer (a) starting from a mixture (A) selected from the group consisting of a mixture comprising at least two isomers of a $C_{16}$ or higher conjugated unsaturated fatty acid and a mixture comprising at least two cis-isomers of a $C_{16}$ or higher unsaturated fatty acid having a double bond involved in the cis-configuration thereof, wherein the method comprises a step of mixing the mixture (A) with at least one $C_4$-$C_{14}$ saturated fatty acid (B) to thus form a mixed solution containing the desired isomer (a) dissolved therein; a crystallization and precipitation step in which crystals enriched with the isomer (a) are separated from the mixed solution or crystals having the reduced concentration of the isomer (a) are separated from the mixed solution; and a solid-liquid separation step for recovering crystals enriched with the isomer (a) or for removing the crystals having the reduced concentration of the isomer (a) to thus recover a solution enriched with the isomer (a).

2. A method for preparing a concentrate which is enriched with a desired isomer (a1) and a concentrate which is enriched with a desired isomer (a2) starting from a mixture (A) selected from the group consisting of a mixture comprising at least two isomers of a $C_{16}$ or higher conjugated unsaturated fatty acid and a mixture comprising at least two cis-isomers of a $C_{16}$ or higher unsaturated fatty acid having a double bond involved in the cis-configuration thereof, wherein the method comprises a step of mixing the mixture (A) with at least one $C_4$-$C_{14}$ saturated fatty acid (B) to thus form a mixed solution containing the desired isomers (a1) and (a2) dissolved therein; a crystallization and precipitation step in which crystals enriched with the isomer (a1) and having the reduced concentration of the isomer (a2) are separated from the mixed solution or crystals enriched with the isomer (a2) and having the reduced concentration of the isomer (a1) are separated from the mixed solution; and a solid-liquid separation step for recovering crystals enriched with the isomer (a1) and having the reduced concentration of the isomer (a2) and a solution enriched with the isomer (a2) and having the reduced concentration of the isomer (a 1), or for recovering the crystals enriched with the isomer (a2) and having the reduced concentration of the isomer (a1) and a solution enriched with the isomer (a1) and having the reduced concentration of the isomer (a2).

3. The method of claim 1, wherein it further comprises an additional step of removing the saturated fatty acid (B) after the solid-liquid separation step.

4. The method of claim 1, wherein an organic solvent is used in the step of mixing the mixture (A) with at least one saturated fatty acid (B).

5. The method of claim 4, wherein it further comprises an additional step of removing the organic solvent and the saturated fatty acid (B) after the solid-liquid separation step.

6. The method of claim 1, wherein the mixing ratio of the mixture (A) and the at least one saturated fatty acid (B) corresponds to not less than one parts by mass of the latter (B) per 100 parts by mass of the mixture (A).

7. The method of claim 1, wherein the isomer (a) the is an unsaturated fatty acid having a cis-configuration existing at any position between the 4-position and the 16-position thereof.

8. The method of claim 1, wherein the position of the cis-configuration of the mixture (A) is different from that of the isomer (a) by not less than 2 positions.

9. The method claim 1, wherein the mixture (A) comprises at least two isomers of conjugated linoleic acid.

10. The method of claim 1, wherein the mixture (A) comprises 9-cis, 11-trans conjugated linoleic acid and 10-trans, 12-cis conjugated linoleic acid.

11. The method of claim 1, wherein the saturated fatty acid (B) is $C_6$-$C_{14}$ saturated fatty acid.

12. The method of claim 1, wherein the saturated fatty acid (B) is a $C_8$ or $C_{10}$ saturated fatty acid.

13. The method of claim 1, wherein the isomer (a) is a conjugated linoleic acid.

14. The method of claim 1, wherein the isomer (a) is 9-cis,11-trans conjugated linoleic acid or 10- trans,12-cis conjugated linoleic acid.

15. A method for preparing a concentrate which is enriched with an isomer (a) wherein the following steps are repeated over at least one time:
a step for mixing a concentrate prepared according to a method as set forth in claim 1 with at least one saturated fatty acid (B) and/or an organic solvent to form a mixed solution containing the isomer (a) dissolved therein;
a crystallization step for precipitating crystals enriched with the isomer (a) or crystals having the reduced concentration of the isomer (a), from the mixed solution; and
a solid-liquid separation step for recovering the crystals enriched with the isomer (a) or for removing the crystals having the reduced concentration of the isomer (a) to thus recover a solution enriched with the isomer (a), wherein the method may further comprise a step of removing the saturated fatty acid (B) and/or the organic solvent after the solid-liquid separation step.

16. A method for preparing a concentrate which is enriched with an isomer (a1) and a concentrate which is enriched with an isomer (a2) wherein the following steps are repeated over at least one time:
a step for mixing a concentrate prepared according to a method as set forth in claim 2 with at least one saturated fatty acid (B) and/or an organic solvent to form a mixed solution containing the isomers (a1) and (a2) dissolved therein;
a crystallization step for precipitating crystals enriched with the isomer (a1) and having the reduced concentration of the isomer (a2) or crystals enriched with the isomer (a2) and having the reduced concentration of the isomer (a1), from the mixed solution; and
a solid-liquid separation step for recovering the crystals enriched with the isomer (a1) and having the reduced concentration of the isomer (a2) and a solution enriched with the isomer (a2) and having the reduced concentration of the isomer (a1), or for removing the crystals enriched with the isomer (a2) and having the reduced concentration of the isomer (a1) and a solution enriched with the isomer (a1) and having the reduced concentration of the isomer (a2), wherein the method may further comprise a step of removing the saturated fatty acid (B) and/or the organic solvent after the solid-liquid separation step.

17. The method of claim 4, wherein the organic solvent is acetone or hexane.

18. The method of claim 1, wherein the concentration of the saturated fatty acid (B) in the mixture (A) is not more than 20% by mass.

19. A method for preparing an ester comprising the step of esterifying a compound having at least one alcoholic hydroxyl group in the molecule with a condensate of an unsaturated fatty acid prepared according to the method of claim 1.

20. The method of claim 19, wherein the compound having at least one alcoholic hydroxyl group in the molecule is glycerin.

* * * * *